(12) United States Patent
Beaulé

(10) Patent No.: US 8,328,816 B2
(45) Date of Patent: Dec. 11, 2012

(54) FEMORAL GAUGE

(75) Inventor: Paul E. Beaulé, Ottawa (CA)

(73) Assignee: Wright Medical Technology, Inc., Arlington, TN (US)

( * ) Notice: Subject to any disclaimer, the term of this patent is extended or adjusted under 35 U.S.C. 154(b) by 1292 days.

(21) Appl. No.: 11/458,756

(22) Filed: Jul. 20, 2006

(65) Prior Publication Data
US 2007/0227024 A1 Oct. 4, 2007

Related U.S. Application Data

(60) Provisional application No. 60/700,828, filed on Jul. 20, 2005.

(51) Int. Cl.
*G01B 1/00* (2006.01)
(52) U.S. Cl. .......................... 606/102; 33/512
(58) Field of Classification Search .............. 33/501, 33/511, 512, 561.1–561.3; 606/102; 623/22.11–22.19
See application file for complete search history.

(56) References Cited

U.S. PATENT DOCUMENTS

| | | | | |
|---|---|---|---|---|
| 763,211 A * | 6/1904 | Shepardson | ........................ | 33/42 |
| 1,255,251 A * | 2/1918 | Waters | ............................. | 33/483 |
| 4,123,806 A * | 11/1978 | Amstutz et al. | ............ | 623/22.39 |
| 4,433,686 A * | 2/1984 | Charnley | .................... | 606/86 R |
| 4,517,969 A * | 5/1985 | Halcomb et al. | ............. | 606/102 |
| 4,950,297 A * | 8/1990 | Elloy et al. | ................. | 623/20.29 |
| 4,974,331 A * | 12/1990 | Watterson | ..................... | 33/514.2 |
| 4,987,904 A * | 1/1991 | Wilson | ........................... | 600/587 |
| 6,197,032 B1 * | 3/2001 | Lawes et al. | ..................... | 606/91 |
| 6,572,655 B1 * | 6/2003 | Johnson | ..................... | 623/22.36 |
| 7,527,631 B2 * | 5/2009 | Maroney et al. | ............. | 606/102 |
| 2003/0114859 A1 * | 6/2003 | Grusin et al. | ................... | 606/87 |
| 2004/0193175 A1 * | 9/2004 | Maroney et al. | ............. | 606/102 |
| 2005/0000104 A1 * | 1/2005 | Arnin | ............................ | 33/555.1 |
| 2005/0033447 A1 * | 2/2005 | Evans | ........................ | 623/23.12 |

OTHER PUBLICATIONS

Beaule, P.E., "A Soft Tissue-Sparing Approach to Surface Arthroplasty of the Hip", Operative Techniques in Orthopaedics, Apr. 2004, 14(2):75-84.

* cited by examiner

*Primary Examiner* — Kevin T Truong
*Assistant Examiner* — Christopher Beccia
(74) *Attorney, Agent, or Firm* — Duane Morris LLP

(57) ABSTRACT

A femoral gauge for sizing a femoral head implant and locating osteophytes or structural abnormalities comprising a gauge portion, the gauge portion having a concave gauge surface and an opposing back surface, the gauge surface defined by a pair of opposing lengthwise sides and a pair of widthwise sides, the gauge surface having a substantially spherical contour, the spherical contour sized for selection of a correspondingly sized femoral head implant, and a handle portion extending from the gauge portion, the handle portion positioned and configured for use in positioning the gauge surface. A plurality of different sized gauges can be provided. Areas of potential infringement can be located by rotating the femoral gauge around the juncture of the natural or implant femoral head and the natural femoral neck. Areas of impingement are removed until the femoral gauge can be rotated around the juncture without lifting off of the femoral head.

10 Claims, 5 Drawing Sheets

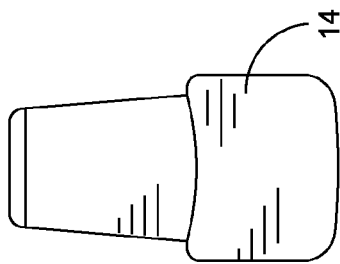
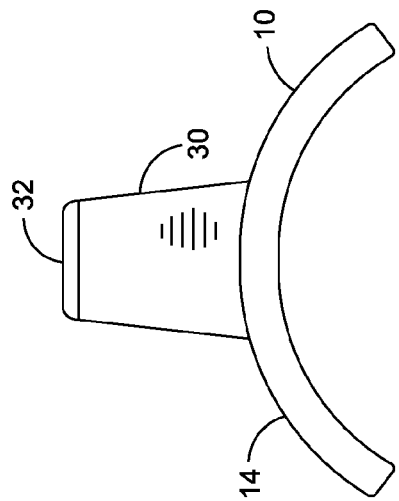
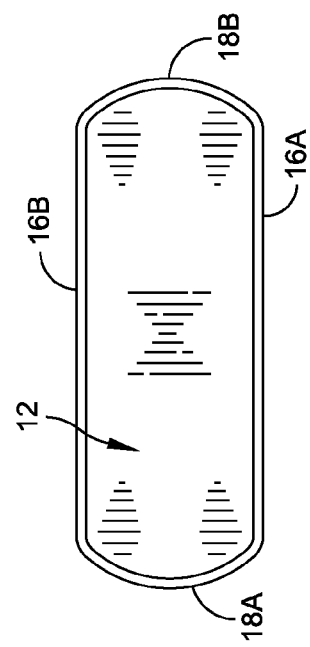
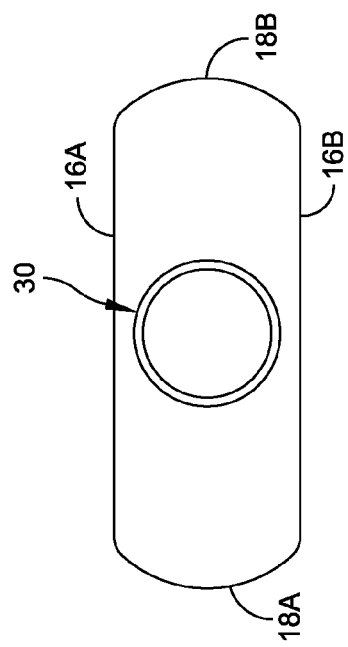

FEMORAL GAUGE

CROSS REFERENCE TO RELATED APPLICATIONS

This application is a continuation of and claims priority to U.S. Provisional Patent Application Ser. No. 60/700,828, filed Jul. 20, 2005.

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to hip surgery, and more particularly to instruments for use in sizing femoral head implants for use in conservative intra-articular hip procedures.

BACKGROUND OF THE INVENTION

In recent years, efforts have been made to develop instruments and procedures for use in minimally invasive hip arthroplasty procedures. In minimally invasive surgical ("MIS") procedures, the operation is carried out through a small incision, such as an 8 cm incision. MIS procedures may reduce trauma to the patient's muscles and other tissues, and typically result in shorter patient recovery time. However, operating in the confines of a small incision presents challenges to the surgeon. The surgeon must often rely on specialized surgical instruments in order to access or operate within the surgical site.

In addition to MIS procedures, efforts have been made to develop bone conserving hip arthroplasty procedures. In conventional total hip arthroplasty, the head and neck of the natural femur are removed and replaced with an artificial femoral head and neck. The artificial head and neck are attached to a stem that is secured in the intramedullary canal of the femur. Over the years, total hip arthroplasty has had excellent clinical success. However, various conditions can arise in which it becomes necessary to perform revision surgery on the hip joint. The presence of the implant in the femur can sometimes result in stress shielding, osteolysis or other conditions that lead to the gradual loss of bone stock and loosening of the implant. An infection may require removal of the implant. Additionally, the useful life of an artificial hip joint is about 15 to 25 years, and a young hip patient will therefore typically require a revision surgery at some point in his or her lifetime.

When performing a revision hip procedure, it is desirable to have as much bone stock available as possible. Accordingly, efforts have been made to develop surface replacement arthroplasty procedures that preserve bone stock in hip procedures. In surface replacement arthroplasty of the hip, the natural femoral head and neck are preserved, but are resurfaced to receive an artificial femoral head. An example of such a femoral head for use in surface replacement arthroplasty procedures is shown in FIGS. 1, 2, 7 and 8 of U.S. Pat. No. 6,156,069 (Amstutz), which is incorporated herein by reference. As shown in FIG. 1 of Amstutz, the femoral head includes a central tapered stem and a spherical surface replacement portion. An inner surface of the prosthesis covers the reamed bone of the femoral head, while the central tapered stem is centered in the femoral head and neck. Femoral heads of the type shown in Amstutz are available from applicant, Wright Medical Technology, Inc. 5677 Airline Road, Arlington, Tenn. 38002.

Instruments have been designed for measuring a patient's femoral head. U.S. Pat. No. 4,517,969, (Halcomb, III et al.) discloses a prosthetic gauge which is used for evaluating the fit of a prosthetic device against a receiving bone or cartilage surface. The gauge includes a portion for gripping and a contact portion extending from the gripping portion. The surface of the contact portion is predeterminedly contoured to conform substantially to the shape of the receiving bone or cartilage surface to be evaluated. The contact surface is a frosted or translucent surface which transmits and diffuses light so that the specific bone or cartilage surface being observed through the gauge cannot be seen clearly until actual contact is made between the contact surface and the articular surface. This aids the surgeon in more accurately determining the apparent contact area, and hence in evaluating the potential fit of the prosthesis. The Holcomb gauge is described primarily with reference to an acetabular gauge, but the patent mentions that the principles can be applied to any suitable prosthetic gauge, and notes that a concave hemispherical, translucent contact surface could be used to measure the femoral head size.

U.S. Pat. No. 5,070,623 (Barnes) discloses a manually operated gauge for the simultaneous measurement of two orthogonal diameters of a spherical member. The gauge comprises four shaped bars all pivotably connected together about four parallel pivot axes, the bars arranged to enclose a measurement or work space into which the spherical member to be measured may be brought. Two main arms are pivotably joined at one end and each is provided with a pair of orthogonally oriented contact surfaces at the other end, the contact surfaces adapted to arcuately move with their respective arms about the arm-pivot in order to capture a spherical member between them. A scale member is pivotably connected to the free end of one of the arms and an indicator member is pivotably joined to the free end of the other of the arms. The scale member and the indicator member are pivotably connected to each other about an axis aligned along the center line of the gauge while the other ends of the scale member and the indicator member cooperate to indicate the size of the spherical component being measured.

The background section of Barnes, at Col. 1, Lines 41-60, states that instruments for measuring the diameter of spherical prosthetic heads include open-faced templates and contour gauges provided in a range of discrete sizes so that the surgeon must select the gauge closest in size to the actual head being measured. Barnes further notes that some spherical head gauges are available as a set of discretely sized, closed circular openings which are used by matching the head being measured to the circular opening having the best fit. Barnes states that these types of gauges are analogous to the aforementioned contour gauges, but that the contour gauge only provides an arcuate portion of a particular circular opening while the circular gauge provides the entire circular opening.

US 2004/10193175 A1 (Maroney) discloses a femoral gauge for measuring the contour of the femur for use in hip arthroplasty (see particularly FIG. 25). The gauge includes a body and a probe. The body has a body contact portion of the body for contact with the femur. The probe is movably positional with respect to the body. The probe includes a contact portion of the probe for contact with the femur. The relative position of the probe with respect to the body is indicative of the femur contour of the femur.

OBJECTS AND SUMMARY OF THE INVENTION

It is an object of the invention to provide instruments and methods for use in sizing femoral head sphericity, particularly in conservative hip procedures such as femoral head/neck recontouring and prosthetic replacement of the articular surface of the femoral head.

It is an object of the invention to provide instruments and methods for locating and removing osteophytes or structural abnormalities from a natural femoral neck in a conservative intra-articular hip procedure.

It is an object of the invention to provide instruments and methods for relieving impingement, reestablishing offset and restoring a pain-free range of motion in hip procedures.

The foregoing and other objects and advantages of the invention are achieved by providing a femoral gauge for selection of an appropriately sized femoral head implant or for locating osteophytes or other structural abnormalities on a natural femoral head and neck, comprising a gauge portion, the gauge portion having a concave gauge surface and an opposing back surface, the gauge surface defined by a pair of opposing lengthwise sides and a pair of widthwise sides, the gauge surface having a substantially spherical contour, the spherical contour sized for selection of a correspondingly sized femoral head implant, and a handle portion extending from the gauge portion, the handle portion positioned and configured for use in positioning the gauge surface.

Each of the opposing lengthwise sides are preferably substantially straight when viewed from above the femoral gauge to thereby allow for visualization of a surface of a femoral head adjacent the gauge portion. The opposing widthwise sides are preferably curved. The handle portion is preferably substantially centered on the back surface of the gauge portion. The handle portion is preferably a generally cylindrical knob. The back surface is preferably spherically convex. The gauge portion may be see-through to thereby allow for visualization through at least a portion of the gauge portion. The gauge surface preferably occupies a lengthwise arc of between about 110 degrees to about 145 degrees and a widthwise arc of between about 20 degrees to about 40 degrees. The lengthwise arc is preferably between about 130 to about 135 degrees. The widthwise arc is preferably about 30 degrees.

The femoral gauges are preferably provided in the form of a kit for use in sizing a femoral head implant in a hip replacement procedure, the kit comprising a set of femoral head implants of sequential sizes and a set of femoral gauges of the type described herein, wherein the spherical contours of the set of femoral gauges are sequentially sized for selection of a correspondingly sized femoral head implant from the set of femoral head implants.

A method of sizing a femoral head implant for resurfacing a natural femoral head of a femur is provided comprising: providing a set of femoral head implants of sequential sizes, and providing a set of femoral gauges of the type described herein, exposing a proximal aspect of the femur, selecting from the set of femoral gauges a gauge that best fits a superior aspect of the natural femoral head, and selecting from the set of femoral head implants a femoral head implant that corresponds to the femoral gauge that best fits the superior aspect of the natural femoral head.

A method is provided for locating and removing osteophytes or structural abnormalities on a natural femoral head and neck junction in order to optimize offset between a femoral head implant and the natural neck and thereby minimize the risk of impingement between the natural femoral neck and an acetabular implant, the method comprising: providing a set of femoral gauges of the type described herein, exposing a proximal aspect of the femur, selecting from the set of femoral gauges a gauge that best fits a superior aspect of a natural femoral head of the femur, rotating the selected femoral gauge around a juncture of the natural femoral head and the natural femoral neck to thereby locate areas of potential impingement between the natural femoral neck and an acetabular implant, and removing the areas of impingement until the femoral gauge can be rotated around the juncture of the natural femoral head and the natural femoral neck without lifting off of the natural femoral head. After a femoral head implant has been secured on the natural femoral neck, the selected femoral gauge can be rotated around a juncture of the femoral head implant and the natural femoral neck to thereby locate areas of potential impingement between the natural femoral head and an acetabular implant. If there are any areas of impingement, the areas of impingement can be removed until the femoral gauge can be rotated around the juncture of the femoral head implant and the natural neck without lifting off of the femoral head implant.

The foregoing and other objects, features, aspects and advantages of the invention will become more apparent from the following detailed description of the invention when considered in conjunction with the accompanying drawings.

BRIEF DESCRIPTION OF THE DRAWINGS

FIG. 2 is a bottom view of one preferred embodiment of a femoral gauge of the invention.

FIG. 3 is top or back view of one preferred embodiment of a femoral gauge of the invention.

FIG. 4 is a side view of one preferred embodiment of a femoral gauge of the invention.

FIG. 5 is a side view of one preferred embodiment of a femoral gauge of the invention, rotated about 90 degrees from FIG. 4.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
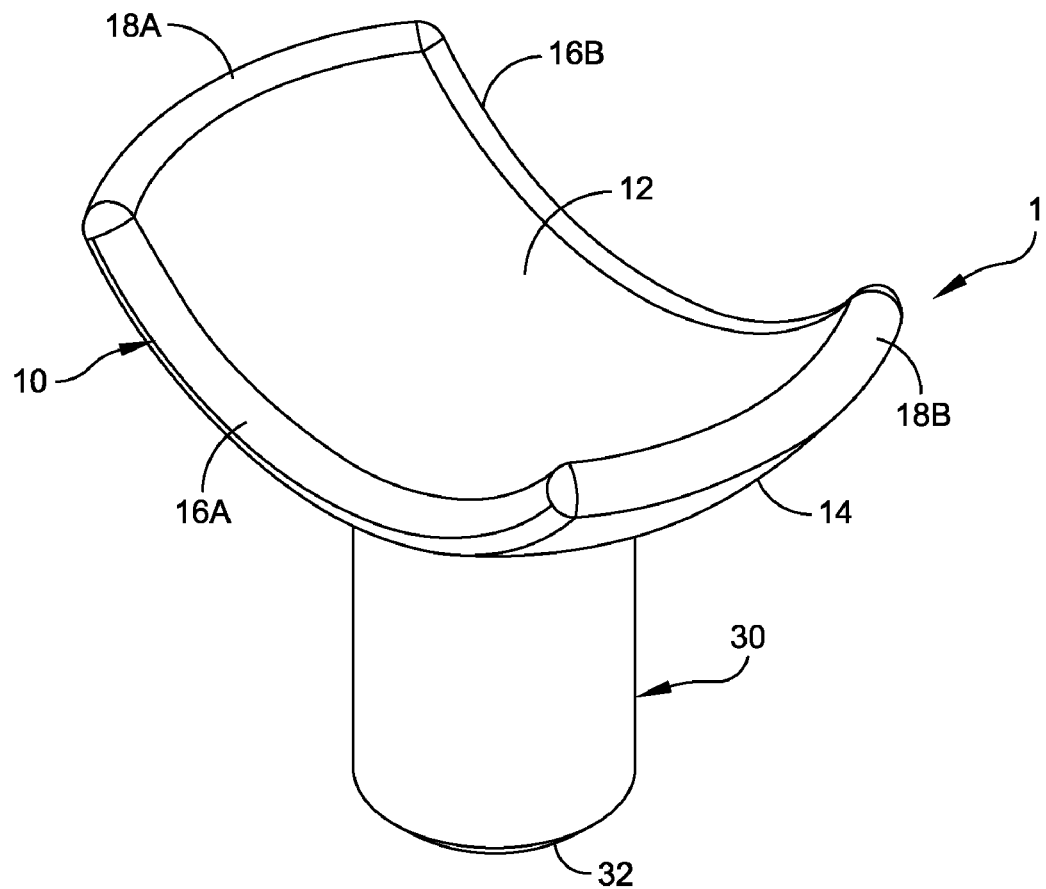
FIG. 1 is a perspective view of one preferred embodiment of a femoral gauge of the invention.

As shown in FIG. 1, the invention includes a femoral gauge 1 for use during surgical intervention on the hip, both for joint preservation and hip resurfacing arthroplasty. As will be described in further detail below, the femoral gauge 1 is used to select an appropriately sized femoral head implant 200.

The femoral gauge 1 can also be used to locate osteophytes or other structural abnormalities 108 on a natural femoral head and neck.

As shown in FIG. 1, the femoral gauge 1 includes a gauge portion 10. The gauge portion 10 has a concave gauge surface 12 and an opposing back surface 14. As shown in FIG. 2, the gauge surface 12 is defined by a pair of opposing lengthwise sides 16A, 16B and a pair of widthwise sides 18A, 18B. As indicated in FIGS. 1 and 4, the gauge surface 12 has a substantially spherical contour. "Substantially spherical" includes spherical as well as moderate deviations from spherical that do not compromise the ability of the gauge 10 to size sphericity of a femoral head 100. The spherical contour of the gauge surface 12 is sized for selection of a correspondingly sized femoral head implant 200, as will be described in further detail below. In a preferred embodiment shown in FIGS. 1 and 4, the back surface 14 of the gauge 1 is spherically convex, a configuration that minimizes the size of the gauge 1 along with the amount of material required to manufacture the gauge 1.

The gauge portion 10 is preferably see-through (transparent or translucent) to thereby allow for visualization through at least a portion of the gauge portion 10. A see-through gauge portion 10 allows a user to view underlying structures when viewing the femoral gauge 1 from the back surface 14. The gauge portion 10 can alternatively be formed from an opaque material, such as metal.

As shown in FIGS. 1, 4 and 5, a handle portion 30 extends from the gauge portion 10. The handle portion 30 is positioned and configured for use in positioning the gauge surface 12, such as on the femoral head 100 or in a juncture between the femoral head 100 and neck 102. In a preferred embodiment shown in FIG. 3, the handle portion 30 is substantially centered on the back surface 14 of the gauge portion 10. In a preferred embodiment shown in FIG. 1, the handle portion 30 is a generally cylindrical knob. "Generally cylindrical" includes cylindrical as well as somewhat tapered or frusto-conical configurations such as the type shown in FIGS. 4 and 5. The handle portion 30 can be provided with a rounded end 32.

Figure 6:
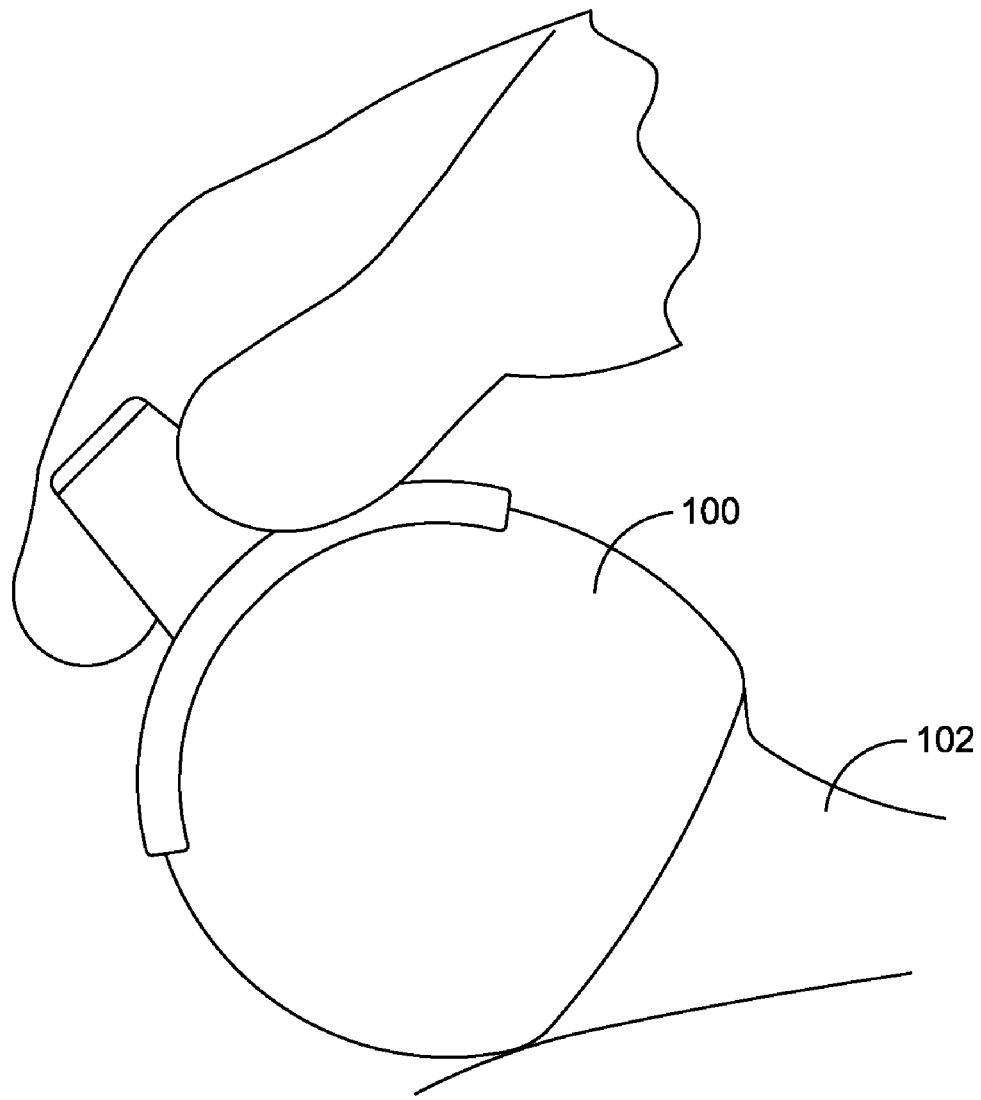
FIG. 6 shows use of one preferred embodiment of the femoral gauge of the invention to size a femoral head.

As shown in FIG. 3, each of the opposing lengthwise sides 16A, 16B are preferably substantially straight when viewed from above the femoral gauge 1. As indicated in FIG. 6, a straight configuration allows for visualization of a surface of a femoral head 100 or neck 102 adjacent the gauge portion 10. In one preferred embodiment shown in FIG. 2, the opposing widthwise sides 18A, 18B are curved. In a preferred embodiment shown in FIG. 1, the opposing lengthwise sides 16A, 16B and the opposing widthwise sides 18A, 18B have rounded edges. The edges of the sides 16A, 16B, 18A, 18B can alternatively be straight, angled or of other configurations.

The lengthwise configuration of the femoral gauge 1 allows it to be used through minimal incisions. The size of the arcs in the lengthwise dimension (i.e. along sides 16A, 16B) and in the widthwise dimension (i.e. along sides 18A, 18B) are selected for use in minimal incisions. The lengthwise arc is preferably between about 110 and about 145 degrees, and is most preferably about 130 to 135 degrees. The widthwise arc is preferably between about 20 and about 40 degrees, and is most preferably about 30 degrees. By providing a gauge portion 10 that occupies only a section of a full spherical dome, the surgeon can maneuver the femoral gauge within the confines of a minimal incision, and can rotate, slide or otherwise manipulate the gauge 1 as needed in order to carry out the objectives of the invention. Additionally, by providing a gauge portion 10 that occupies only a portion of a full spherical dome, the gauges 1 take up less space in an operating kit, which facilitates packaging and reduces shipping costs. The size, configuration and placement of the handle portion 30 also assist the surgeon in inserting the gauge 1 into a small MIS incision, manipulating the gauge 1 within the incision, and removing the gauge 1 from the incision.

Figures 7A, 7B:
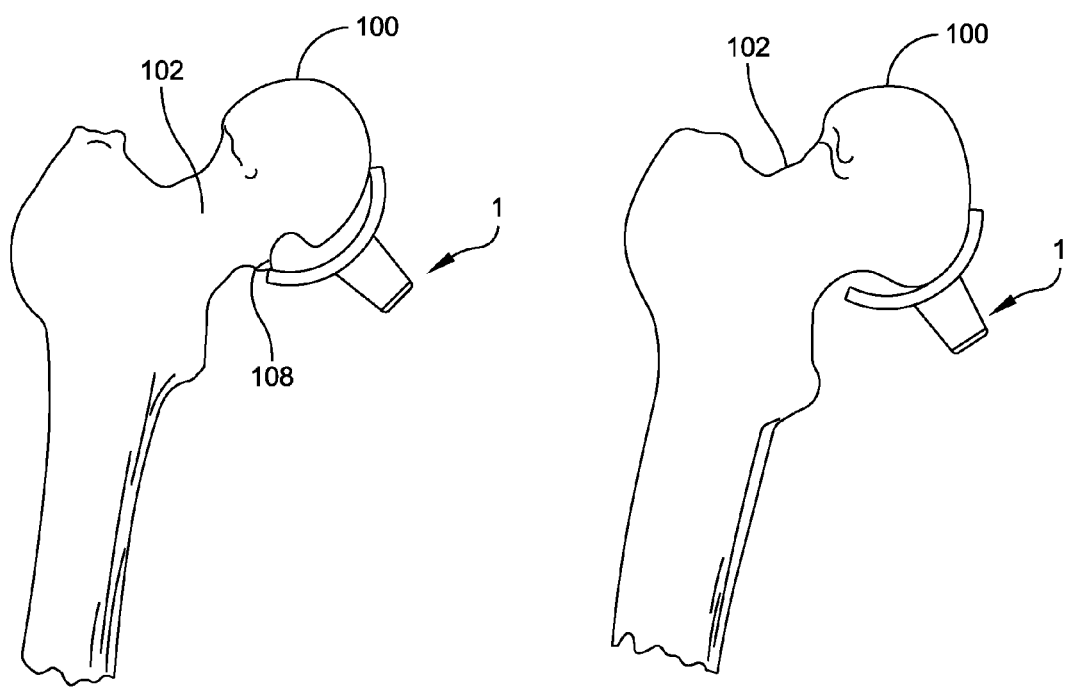
FIG. 7 shows use of one preferred embodiment of the femoral gauge of the invention to locate osteophytes and other areas of impingement between a femoral neck and an acetabular implant.
Figure 8:
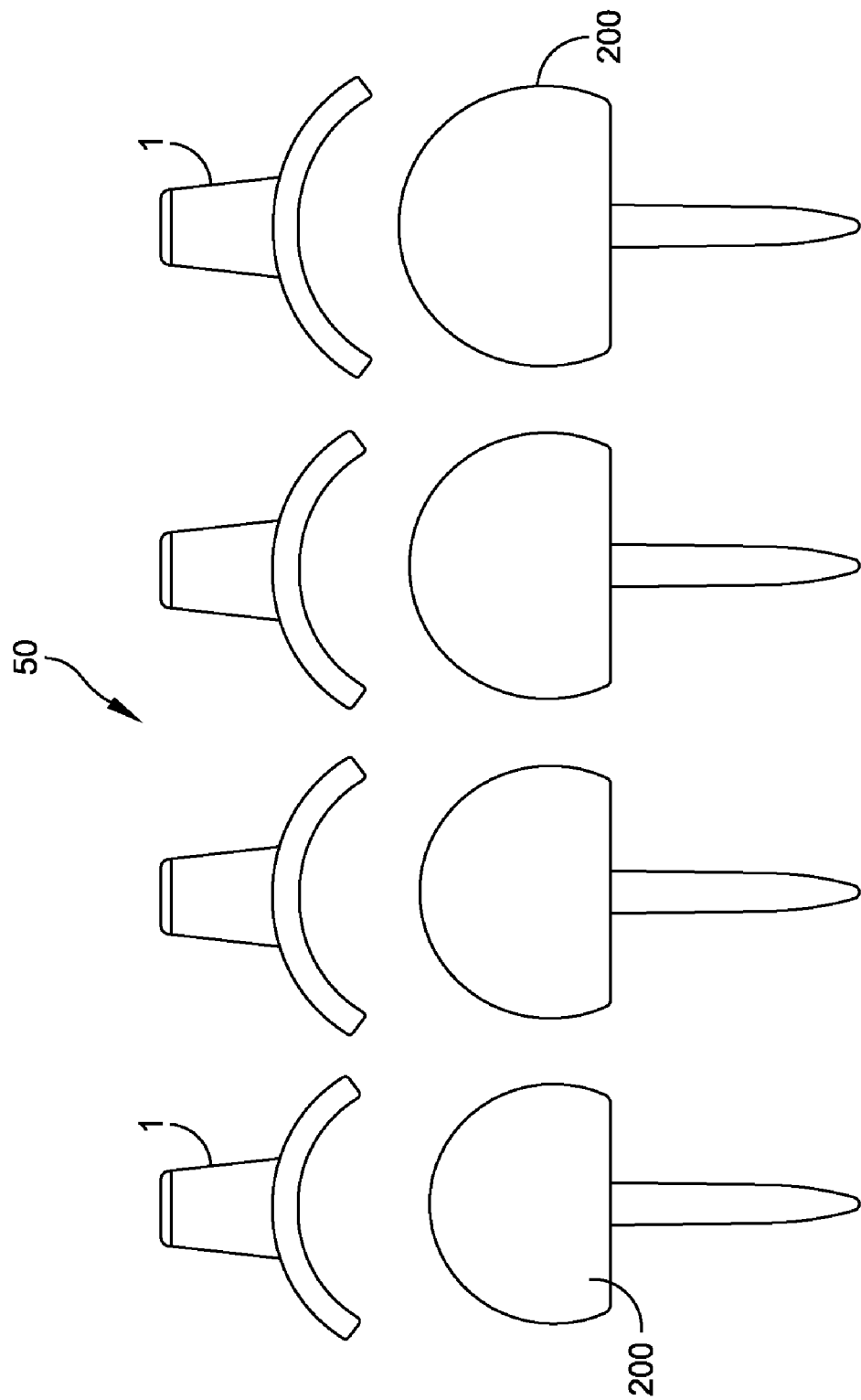
FIG. 8 shows a representative view of a preferred embodiment of a femoral gauge kit according to the invention.

As shown in FIG. 8, the femoral gauge 1 is preferably provided in the form of a kit 50 for use in sizing femoral head implants. A femoral gauge kit 50 includes a set of femoral gauges 1 and a set of femoral head implants 200. Acceptable femoral head implants 200 for use in the kit include the femoral heads shown in FIGS. 1, 2, and 7 of U.S. Pat. No. 6,156,069 (Amstutz), which is incorporated herein by reference. The spherical contours of the gauge surfaces 12 of the set of femoral gauges 1 are sequentially sized for selection of a correspondingly sized femoral head implant 200 from the set of femoral head implants 200. In a preferred embodiment, the sequential sizes of the femoral head implants 200 are 36 mm, 38 mm, 40 mm, 42 mm, 44 mm, 46 mm, 48 mm, 50 mm, 52 mm and 54 mm in diameter, and the sequential sizes of the spherical contours of the gauge surfaces 12 are, correspondingly, 36 mm, 38 mm, 40 mm, 42 mm, 44 mm, 46 mm, 48 mm, 50 mm, 52 mm and 54 mm in diameter. The components of the kit can also be provided in other selected increments, such as 1 mm. A labeling or matching system is preferably provided so that the surgeon can readily select the femoral head implant 200 that corresponds to the selected femoral gauge 1. The components of the kit are preferably arranged in a convenient format, such as in a surgical tray or case. However, the kit components do not have to be packaged or delivered together, provided that they are assembled or collected together in the operating room for use at the time of surgery.

In operation, the femoral gauge 1 is used to select the appropriately sized femoral head sphericity and implant 200. The surgeon is preferably provided with a kit 50 of the type described above, containing a set of femoral head implants 200 and femoral gauges 1. As shown in FIG. 6, after exposing a proximal aspect of the femur, the surgeon selects a femoral gauge 1 that best fits a superior aspect of the natural femoral head 100. The surgeon then selects a femoral head implant 200 that corresponds to the femoral gauge 1 that best fits the superior aspect of the natural femoral head 100. Based on the sizing, the surgeon then reams the natural femoral head 100 to an appropriate size for receiving the selected femoral head implant 200. Reaming is preferably carried out by placing an appropriate cylindrical reamer having the same size as the gauge 1 onto the femoral head at a valgus orientation from the anatomical neck of the femur, i.e. 5-10 degrees. This technique allows for selection of an implant 200 size that most closely reproduces the patient's anatomy, which provides optimal sizing of components and minimizes the risk of femoro-acetabular impingement.

As shown in FIGS. 7A and 7B, the femoral gauge 1 can also be used to locate and remove osteophytes or structural abnormalities on the natural femoral neck 102 in order to optimize offset between the femoral head implant 200 and the natural neck 102, and thereby minimize the risk of impingement between the natural femoral neck and an acetabular implant 220. Impingement of the neck with the acetabular component could lead to acetabular 220 loosening, erosion of bone, and persistent groin pain. In a preferred method, the surgeon locates and removes osteophytes after sizing the femoral head 100. Using the femoral gauge 1 size that best fits a superior aspect of the natural femoral head 100 of the femur, the surgeon rotates the selected femoral gauge 1 around a juncture of the natural femoral head 100 and the natural femoral neck 102 to thereby locate areas of potential impingement 108 between the natural femoral neck 102 and an acetabular implant 220. By rotating the femoral gauge 1, the surgeon mimics the probable path of an acetabular implant 220 around the juncture of the femoral head implant 200 and the natural femoral neck 102. As indicated in FIG. 7A, areas of impingement 108 are located by observing where the gauge portion 10 lifts away from the femoral head 100 due to an encounter with an obstruction 108 on the neck 102. The area of bone resection can be marked at the point where the gauge 1 lifts off when rotated from its starting position at the dome of the femoral head 100 and going down towards the neck 102. As indicated in FIG. 7B, the surgeon removes the areas of impingement 108 until the femoral gauge 1 can be rotated around the juncture of the natural femoral head 100 and the natural femoral neck 102 without lifting off of the natural femoral head 100.

Once the femoral head implant 100 has been secured on the natural femoral neck 102, the surgeon preferably rotates the femoral gauge 1 around the juncture of the femoral head implant 200 and the natural femoral neck 102 to verify that all likely impingements 108 have been removed. If any areas of impingement remain 108, they are removed. Alternatively, the step of removing impingements 108 can be carried out after the femoral head implant 200 has been implanted.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A femoral gauge for selection of an appropriately sized femoral head implant, said femoral gauge also useable for locating osteophytes or other structural abnormalities on a natural femoral head and neck, comprising:

a gauge portion, said gauge portion having a concave gauge surface and an opposing back-surface, said gauge surface defined by a pair of opposing lengthwise sides and a pair of widthwise sides, each of said opposing lengthwise sides are substantially straight when viewed from above said femoral gauge to thereby allow for visualization of a surface of a femoral head adjacent said gauge portion, said gauge surface having a substantially spherical contour, said spherical contour sized for selection of a correspondingly sized femoral head implant, and a handle portion extending from said gauge portion, said handle portion positioned and configured for use in positioning said gauge surface.

2. The femoral gauge of claim 1, wherein said opposing widthwise sides are curved.

3. The femoral gauge of claim 1, wherein said handle portion is substantially centered on said back surface of said gauge portion.

4. The femoral gauge of claim 3, wherein said handle portion is a generally cylindrical knob.

5. The femoral gauge of claim 1, wherein said back surface is spherically convex.

6. The femoral gauge of claim 1, wherein said gauge portion is see-through to thereby allow for visualization through at least a portion of said gauge portion.

7. The femoral gauge of claim 1, wherein said gauge surface occupies a lengthwise arc of between about 110 degrees to about 145 degrees and a widthwise arc of between about 20 degrees to about 40 degrees.

8. The femoral gauge of claim 7, wherein said lengthwise arc is between about 130 to about 135 degrees.

9. The femoral gauge of claim 7, wherein said widthwise arc is about 30 degrees.

10. The femoral gauge of claim 1, wherein the gauge portion is formed from a transparent or translucent material.

\* \* \* \* \*